US006627786B2

(12) United States Patent
Roe et al.

(10) Patent No.: US 6,627,786 B2
(45) Date of Patent: Sep. 30, 2003

(54) WEARABLE ARTICLE HAVING A WETNESS SENSATION MEMBER

(75) Inventors: Donald C. Roe, West Chester, OH (US); Patrick J. Allen, Cincinnati, OH (US); Edward P. Carlin, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/994,461

(22) Filed: Nov. 26, 2001

(65) Prior Publication Data

US 2003/0100872 A1 May 29, 2003

(51) Int. Cl.$^7$ ................................................ A61F 13/15
(52) U.S. Cl. .................. 604/361; 604/385.08; 604/378
(58) Field of Search ........................... 604/361, 385.01, 604/378, 385.08

(56) References Cited

U.S. PATENT DOCUMENTS

| | | | |
|---|---|---|---|
| 3,794,024 A | | 2/1974 | Kokx et al. |
| 4,022,210 A | * | 5/1977 | Glassman |
| 4,022,211 A | | 5/1977 | Timmons et al. |
| 4,106,001 A | | 8/1978 | Mahoney |
| 4,963,139 A | * | 10/1990 | Dabroski |
| 5,266,592 A | | 11/1993 | Grub et al. |
| 5,277,180 A | | 1/1994 | Angelillo et al. |
| 5,342,343 A | | 8/1994 | Kitaoka et al. |
| 5,649,914 A | | 7/1997 | Glaug et al. |
| 5,658,268 A | | 8/1997 | Johns et al. |
| 5,681,298 A | | 10/1997 | Brunner et al. |
| 5,702,376 A | | 12/1997 | Glaug et al. |
| 5,728,125 A | | 3/1998 | Salinas |
| 5,846,230 A | | 12/1998 | Osborn, III et al. |
| 5,885,264 A | | 3/1999 | Matsushita |
| 5,891,124 A | | 4/1999 | Nomura et al. |
| 5,947,947 A | | 9/1999 | Tanzer et al. |
| 6,114,597 A | * | 9/2000 | Romare |
| 6,146,367 A | | 11/2000 | Otsubo et al. |
| 6,169,225 B1 | | 1/2001 | Otsubo |
| 6,200,668 B1 | | 3/2001 | Kronzer |
| 6,229,063 B1 | | 5/2001 | Shimoe et al. |
| 6,320,096 B1 | | 11/2001 | Inoue et al. |

FOREIGN PATENT DOCUMENTS

| | | |
|---|---|---|
| EP | 0 861 645 A2 | 9/1998 |
| EP | 0 904 758 A2 | 3/1999 |
| EP | 0 919 213 A2 | 6/1999 |

* cited by examiner

Primary Examiner—Dennis Ruhl
(74) Attorney, Agent, or Firm—Michael P. Hayden; Jay A. Krebs; Ken K. Patel (57) ABSTRACT

A wearable article useful for facilitating toilet training is provided. The wearable article includes a wetness sensation member held in close contact with a wearer's skin during use that enhances the wearer's awareness that urination has occurred. The wetness sensation member includes a permeable layer and an impermeable layer. During insults of urine, the permeable layer allows urine to penetrate in the z-direction and provides a medium for the flow of urine in the x-y plane via wicking. The impermeable layer supports the flow of liquid between the permeable and impermeable layers and retains the liquid thereby increasing the wetted area contacting the wearer's skin.

12 Claims, 8 Drawing Sheets

WEARABLE ARTICLE HAVING A WETNESS SENSATION MEMBER

FIELD OF THE INVENTION

This invention is directed to hygienic absorbent articles, such as diapers, training pants and the like. Particularly, the invention is directed to training pants facilitating the toilet training process.

BACKGROUND OF THE INVENTION

Absorbent articles are well known in the art. These articles typically have an absorbent core held or positioned in proximity to the body of a wearer during use by a fastening system in order to capture and absorb bodily exudates discharged from the wearer. Typical absorbent articles include a topsheet facing the wearer, which permits fluid exudates to pass through, and a backsheet, which prevents the exudates from escaping from the absorbent article.

Disposable absorbent articles such as diapers are designed to absorb and contain bodily waste in order to prevent soiling of the body and clothing of the wearer. The disposable diapers typically comprise a single design available in different sizes to fit a variety of wearers ranging from newborns to toddlers undergoing toilet training. The design of the diaper typically affects performance, such as, ability to absorb and contain bodily waste. The size of the diaper typically affects fit, for example, the size of the diaper waist opening, the size of the openings around the thighs, and the length or "pitch" of the diaper.

The toilet training stage may be referred to as the "point of exit" as toddlers typically leave the product category once training is successfully completed. The age at which children are toilet trained in "developed" countries has increased steadily over the past several decades and is now in the range of about 24–48 months. One reason toilet training has become delayed is due to significant technical improvements in diaper dryness and comfort. In modern diapers, the child has dry skin even after one or more urinations. As a result, the child feels little or no discomfort and often may not even be aware that they have urinated.

Many parents have the child wear cotton training pants or underwear during toilet training so the child feels discomfort following urination in their "pants". It is believed that such discomfort assists with learning or provides motivation to learn proper toilet training. Cotton training pants leave the skin wet and, due to their high breathability, promote evaporative cooling of the skin, further enhancing discomfort. The current tradeoff in this approach, however, is that cotton training pants have poor urine containment leading to wet clothing and often times, wet surroundings e.g. carpeting, furniture, etc. Clearly there is a need to provide a training signal to the toilet training child while preventing urine leakage and unnecessary changes of clothing.

Thus, it would be desirable to provide a wearable article that can facilitate toilet training by enhancing a wearer's awareness that urination has occurred while at the same time providing the protection of an absorbent article, preventing soiling of the wearer's clothing and surroundings. Particularly, it would be desirable to provide such a wearable article providing an effective signal of urination by ensuring that the wearer feels an uncomfortable wetness sensation resulting from urination.

SUMMARY OF THE INVENTION

In order to solve one or more of the problems found in the art, a wearable article, such as an absorbent article, is provided with a wetness sensation member held in close contact with a wearer's skin during use that enhances the wearer's awareness that a discharge of bodily exudates, such as urine, has occurred. The wetness sensation member comprises a permeable layer and an impermeable layer disposed in a face-to-face arrangement with the permeable layer. The wetness sensation member is typically in proximity to the wearer's urethra so that once the wearer urinates wetting an area of the wetness sensation member, the urine penetrates through the thickness of the permeable layer in the z-direction to the impermeable layer which provides a path of least resistance supporting the flow of urine in the x-y plane. This enables the urine to wet a large area of the wetness sensation member before being absorbed into the absorbent core. The wetness sensation member is held in contact with the wearer's skin during use thereby enhancing the wearer's awareness that urination has occurred.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 5b is a cross sectional view of the diaper illustrated in FIG. 5a.

FIG. 6b is a cross sectional view of the diaper illustrated in FIG. 6a.

FIG. 7b is a cross sectional view of the diaper illustrated in FIG. 7a.

FIG. 8b is a cross sectional view of the diaper illustrated in FIG. 8a.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included drawings.

The present invention provides a wearable article having a wetness sensation member that increases a wearer's awareness that urination has occurred by causing the urine discharged from the body of the wearer to wet an effective area of the member held in close contact with the wearer's skin during use. The wetness sensation member is equally applicable to wearable articles such as disposable absorbent articles including training pants, incontinence briefs, incontinence undergarments, absorbent inserts, diaper holders and liners, feminine hygiene garments, and the like. One embodiment of an absorbent article of the present invention is a unitary disposable absorbent article, such as the disposable diaper 20, shown in FIG. 1. However, preferably, the present invention is applicable to disposable training pants and pull-on diapers designed to facilitate toilet training.

Definitions

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "z-direction" is orthogonal to both the longitudinal and transverse directions.

The "x-y plane refers to the plane congruent with the longitudinal and transverse directions.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

As used herein, the term "impermeable" generally refers to articles and/or elements that are not penetrative by fluid in the liquid state through the entire Z-directional thickness of the article under pressure of 0.14 lb/in$^2$ or less. Preferably, the impermeable article or element is not penetrative by fluid in the liquid state under pressures of 0.5 lb/in$^2$ or less. More preferably, the impermeable article or element is not penetrative by fluid in the liquid state under pressures of 1.0 lb/in$^2$ or less.

Figure 1:
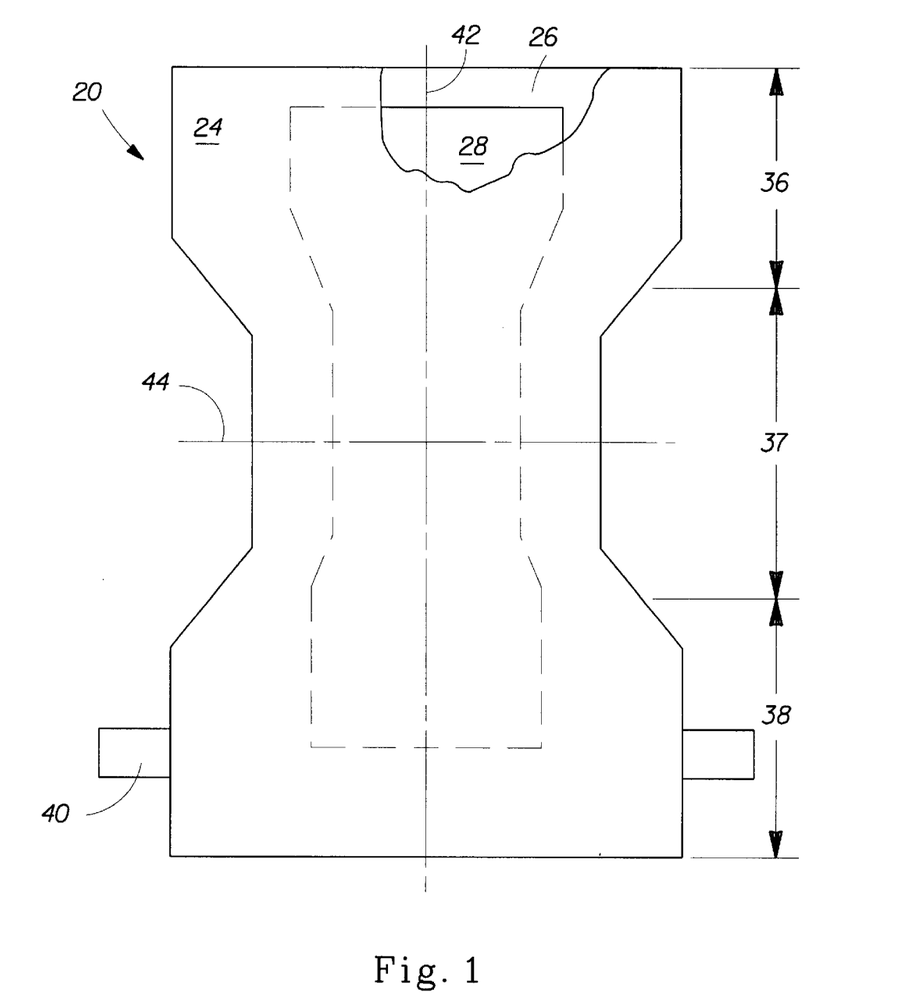
FIG. 1 is a plan view of a disposable diaper.

FIG. 1 is a plan view of the diaper 20 in its flat out, uncontracted state (i.e., without elastic induced contraction) with portions of the structure being cut away to more clearly show the underlying structure of the diaper 20 and with the portion of the diaper 20 which contacts the wearer facing the viewer. The diaper 20 includes a longitudinal axis 42 and a transverse axis 44. One end portion 36 of the diaper 20 is configured as a first waist region of the diaper 20. The opposite end portion 38 is configured as a second waist region of the diaper 20. An intermediate portion 37 of the diaper 20 is configured as a crotch region, which extends longitudinally between the first and second waist regions 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The diaper 20 preferably comprises a liquid pervious topsheet 24, a liquid impervious backsheet 26, and an absorbent core 28 encased between the topsheet 24 and the backsheet 26. The topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The diaper 20 may include a fastener such as a hook and loop type fastening system 40 including at least one engaging component (male fastening component) and at least one landing zone (female fastening component). The diaper 20 may also include such other features as are known in the art including leg cuffs, front and rear ear panels, waist cap features, elastics and the like to provide better fit, containment and aesthetic characteristics. Such additional features are well known in the art and are described in U.S. Pat. Nos. 3,860,003; and 5,151,092, which are incorporated by reference herein.

In addition, the present invention may be suitable for other diaper embodiments including those disclosed in U.S. Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,897,545 titled "Elastomeric Side Panel for Use with Convertible Absorbent Articles" issued Apr. 27, 1999; U.S. Pat. No. 5,904,673 titled "Absorbent Article With Structural Elastic-Like Film Web Waist Belt" issued May 18, 1999; U.S. Pat. No. 5,931,827 titled "Disposable Pull On Pant" issued Aug. 3, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999, the disclosures of which are incorporated herein by reference.

Figure 2:
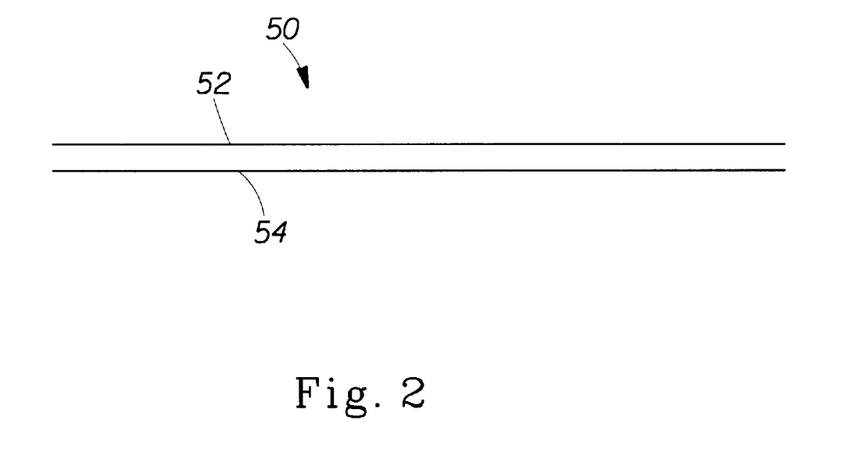
FIG. 2 is a cross sectional view of a wetness sensation member according to the present invention.

An exemplary wetness sensation member according to the present invention is shown in FIG. 2. The wetness sensation member 50 comprises a permeable layer 52 and an impermeable layer 54 disposed opposite the permeable layer 52. The impermeable layer is preferably impermeable to fluid in the liquid state but permeable to vapor so that it is breathable. The wetness sensation member 50 according to the present invention preferably comprises a permeable body-facing layer (upper layer) and an impermeable layer (lower layer) opposite the body facing layer.

During insults of urine, the permeable layer 52 allows urine to penetrate in the z-direction and also provides a medium for the flow of urine in the x-y plane via wicking. The impermeable layer supports the flow of liquid between the permeable and impermeable layers and retains the liquid thereby expanding the wetted area of the wetness sensation member, which is held in as intimate and continuous contact as possible with the wearer's skin. The combination of penetration and flow enables the urine to spread out and effectively wet a large area before being absorbed into the core, which in turn maximizes the wetness signal experienced by the wearer.

Exemplary permeable layers suitable for use in the wetness sensation members of the present invention include nonwovens, foams, woven materials, etc. The permeable layer is preferably hydrophilic and capable of retaining at least 4–12 g/g urine against gravity. Exemplary impermeable layers suitable for use in the wetness sensation members of the present invention include polyolefinic films, microporous or breathable films, other films, and hydrophobic nonwovens having a hydrohead greater than about 0.14 lb/in$^2$. Suitable hydrophobic nonwovens include SM (spunbond meltblown), SMS (spunbond meltblown spunbond), and SMMS (spunbond meltblown meltblown spunbond) composites.

The benefits of the wetness sensation member can be shown by comparison of the strikethrough time for a given sample of temperature sensation member and a topsheet material. Strikethrough is the time required for a given volume of surface applied liquid to enter a given material into an underlying absorbent core. The testing is performed according to Topsheet Strikethrough Time Test provided. The testing was performed comparing a wetness sensation member composed of a 18 g/m$^2$ spunbond nonwoven laminated to a 20 g/m$^2$ SMMS nonwoven via 6 g/m$^2$ adhesive to a topsheet material composed of 18 gsm Spunbond nonwoven. The results of the testing revealed the wetness sensation member to have a strikethrough time on the average about 3.4 times the strikethrough time of the topsheet material. The results of the testing are illustrated in the table below.

| Strikethrough Test | |
|---|---|
| Topsheet Only (sec) | Wetness Sensation Member (Sec) |
| 2.42 | 6.26 |
| 2.44 | 8.93 |
| 2.24 | 7.52 |
| 2.17 | 7.80 |
| 2.11 | 8.05 |
| 2.27 | 8.16 |
| 2.28 | 7.53 |
| 2.54 | 7.76 |
| 2.36 | 8.12 |
| 2.09 | 8.56 |

-continued

| Strikethrough Test | |
|---|---|
| Topsheet Only (sec) | Wetness Sensation Member (Sec) |
| 1.98 | 6.27 |
| Average 2.26 | 7.72 |

Topsheet Strikethrough Time Procedure

Perform the analysis in a room conditioned at 73+2° F. and 50+2% relative humidity. Set up a ring stand to support a clean, automatic filling buret and a separatory funnel so that the tip of the buret extends into the separatory funnel. Position the Plexiglas base plate of the strike-through/rewet apparatus on the base of the ring stand beneath the tip of the separatory funnel so that the tip of the funnel will be 1⅛+1/32 inch above the top of the Plexiglas base plate. Using Tygon tubing, connect the aspirator bottle to the automatic filling buret. Place a magnetic stirring bar in the aspirator bottle. Fill the bottle with synthetic urine test solution (see Solution). Turn on the motor to the magnetic stirrer and keep it on for the duration of the testing. After the test solution has stirred for a minimum of 30 minutes, rinse the buret at least 3 times with the solution before filling to the zero mark. Make sure the buret tip is filled also. Place 15 ml of test solution in the separatory funnel and drain to wet the walls of the funnel. Repeat for a total of two times. The buret must be rinsed at least three times and the walls of the separatory funnel wetted twice, using these techniques, before the beginning of each testing session. These preparation steps are performed only after the test solution has stirred at least 30 minutes.

All testing is done with the test solution in the aspirator bottle under agitation.

NOTE: Keeping the buret full of the test solution when not in use will prevent it from becoming dirty on the inside. Dirty glassware, including the buret, separatory funnel, and strikethrough plate will not drain properly. Once a week, or more often if necessary, clean the buret, the separatory funnel, and the strikethrough plate thoroughly with an Alconox solution. (To prepare Alconox solution, dissolve about eight grams of Alconox in one liter of warm water.) Clean the strikethrough plate cavity, the bottom of the strikethrough plate, the plastic points at the bottom of the cavity, and around and between the electrodes with Alconox solution and a pipe cleaner. Rinse the buret, the separatory funnel, and the strikethrough plate several times with distilled water and then with the test solution before using. All Alconox must be removed before using for further testing.

The amount of test solution used in the strikethrough/rewet test sequence is a characteristic of the lot of Eaton-Dikeman #939 filter paper being used. For each issue of Eaton-Dikeman #939 filter paper provided, the total volume of test solution to be used for the strikethrough/rewet sequence will be specified in terms of an "X-loading" factor, which represents the ml of test solution to be used per g of filter paper stack weight.

To determine the total solution volume to be used in milliliters, multiply the "X-loading" factor by the filter paper stack weight; i.e., if the "X-loading" for a lot of paper is 3.90 ml/g and filter paper stack weight determined was 4.35 g, the total test solution volume required is 3.90×4.35=17.0 ml.

Place the topsheet sample to be tested on a previously weighted 4 in.×4 in. three sheet filter paper stack with the side of the topsheet, which will be next to the baby facing up. Place the total sample filter paper stack and topsheet on the dry Plexiglas base plate with the fabric facing up. (Plexiglas base plate and strikethrough plate must be dried between tests with a Bounty towel.) Center the dry strikethrough plate on the topsheet and center the entire assembly under the stem of the separatory funnel with the tip of the funnel 1⅛+1/32 in. above the top of the Plexiglas base plate.

Strikethrough

With the separatory funnel stopcock closed, discharge 5.0 ml of test solution from the buret into the funnel.

With the strikethrough/rewet apparatus timer power ON, the timer set to zero, and the wires connected to the strikethrough plate, start the test measurement by suddenly opening the funnel stopcock and discharging the 5.0 ml into the strikethrough plate sample cavity. The initial liquid discharge will start the timer and after the liquid has emptied from the cavity, the timer will shut off. After the timer has shut off, record the strikethrough time to the nearest 0.01-second. Do not remove the strikethrough plate, sample pad, etc. from under the separatory funnel. Close the separatory stopcock.

The ability of wetness sensation member to support the flow of liquid in the x-y plane can be measured by its wicking capability. The wicking capability of the wetness sensation member was measured according to INDA Standard test: IST 10.1 (95) Paragraph 10. Liquid Wicking Rate. The test is the measure of the time in seconds for liquid to wick vertically 1.0 inch. The results of the test, summarized in the table below, reveal that wetness sensation member can support vertical wicking of 1.0 inch in an average time of 6.8 seconds whereas the topsheet material was incapable of reaching the 1.0-inch level of vertical wicking.

| | Vertical Wicking Test | |
|---|---|---|
| | Topsheet Only (seconds to 1") | Wetness Sensation Member (seconds to 1") |
| | N/A | 8 |
| | N/A | 7 |
| | N/A | 7 |
| | N/A | 6 |
| | N/A | 7 |
| | N/A | 6 |
| | N/A | 6 |
| | N/A | 7 |
| | N/A | 7 |
| | N/A | 7 |
| Average | N/A | 6.80 |

The wetness sensation member according to the present invention may be arranged in an absorbent article in a variety of configurations. In addition, absorbent articles may include a single wetness sensation member or a plurality of wetness sensation members. In any event, the wetness sensation member(s) are preferably a part of, or attached to, an element or web, such as a topsheet, which is reliably held against the skin of the wearer. In addition, the wetness sensation member(s) are preferably positioned within the absorbent article to enhance the likelihood of being wetted with urine.

Figure 3A:
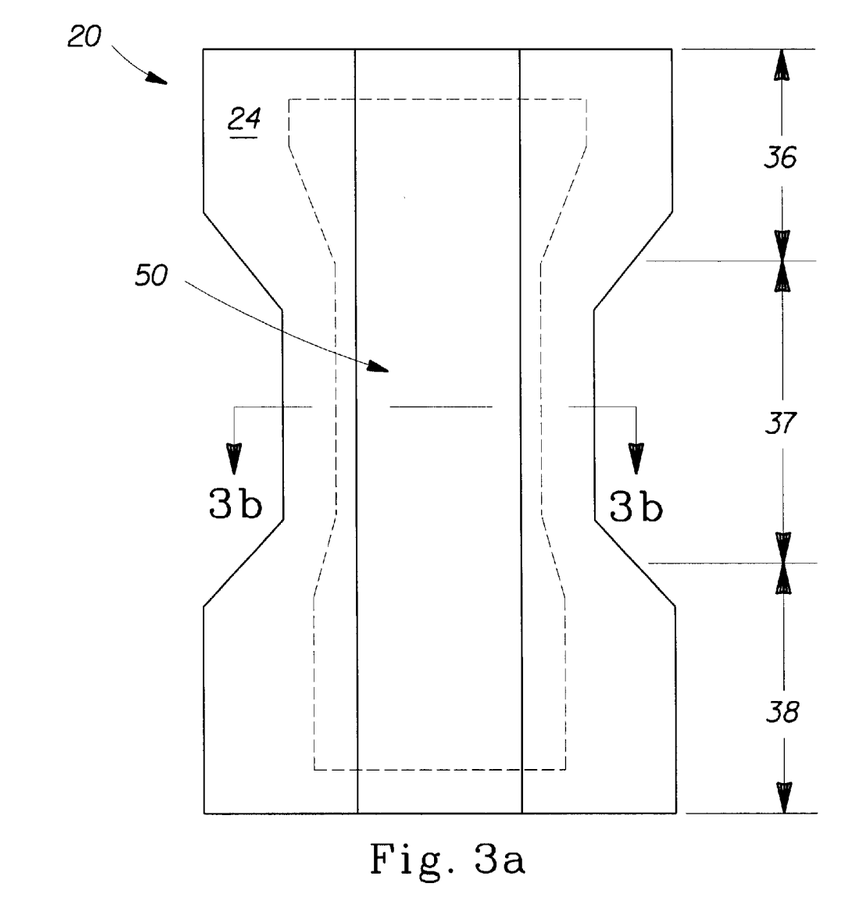
FIG. 3a is a plan view of a diaper having a wetness sensation member disposed on a body-facing surface.
Figure 3B:
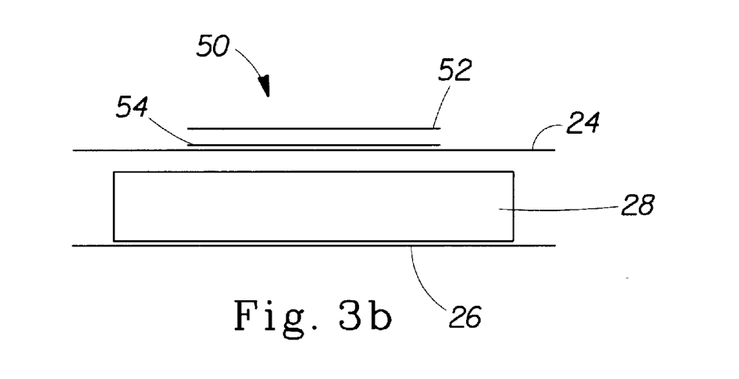
FIG. 3b is a cross sectional view of the diaper shown in FIG. 3a illustrating the layers of the wetness sensation member.

An exemplary embodiment of a wetness sensation member 50 disposed with the topsheet 24 is illustrated in FIGS. 3a and 3b. As shown, the wetness sensation member 50 comprises a separate composite member attached to the topsheet 24. The wetness sensation member 50 comprises a permeable body-facing layer 52, and impermeable layer 54 opposite the body-facing layer. For this embodiment, the wetness sensation member 50 is preferably configured and assembled to enhance the likelihood of making contact with the wearer's skin during use. For instance, the impermeable layer 54 of the wetness sensation member 50 may be bonded to the topsheet 24 using adhesives, ultrasonic bonds, radio frequency bonds, or other suitable means while either the topsheet 24 or the wetness sensation member 50 is elastically foreshortened to deflect the member 50 towards the wearer's skin.

Figure 4:
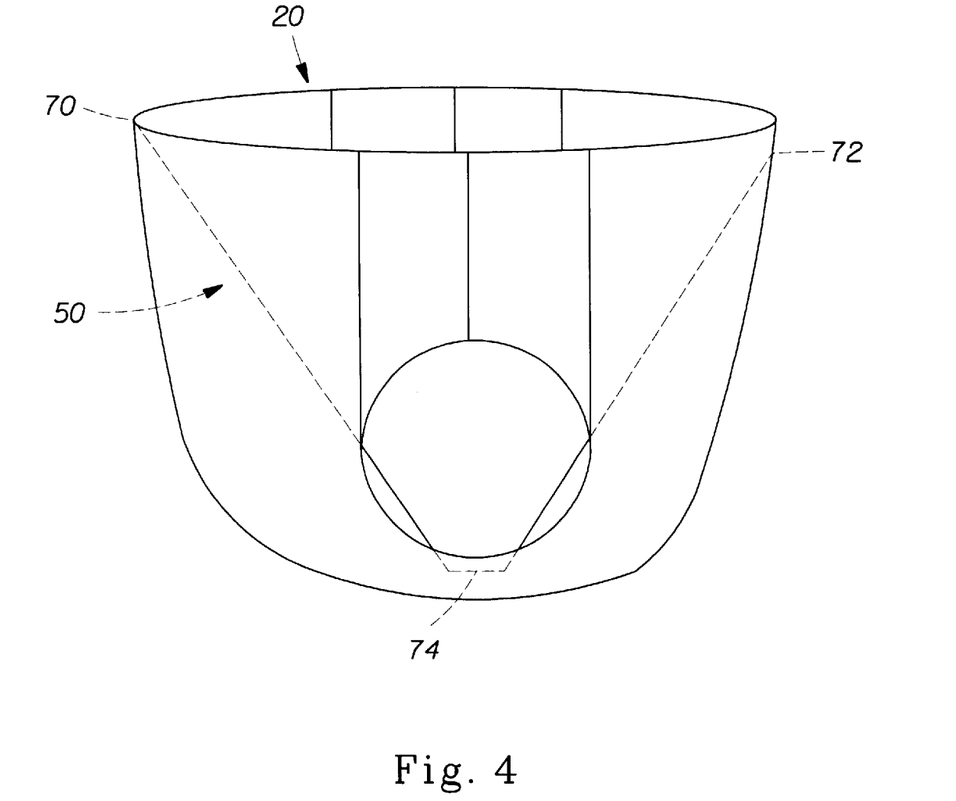
FIG. 4 is an isometric view of a pull-on diaper illustrating the attachment of the wetness sensation member.

In an embodiment illustrated in FIG. 4, a wetness sensation member 50 comprising a separate composite member is disposed on the topsheet 24 of a pull-on type diaper. For this embodiment, the wetness sensation member 50 has elastic properties and includes a first longitudinal end 70 attached to the first waist region 36 and a second longitudinal end 72 attached to the second waist region 38. In addition, a center portion 74 of the member 50 is preferably attached to the crotch region 37 of the diaper 20 in order to stabilize the member and facilitate fitting the article to the wearer, prevent interference with bowel movements and ensure good contact with the wearer's skin.

Figure 5A:
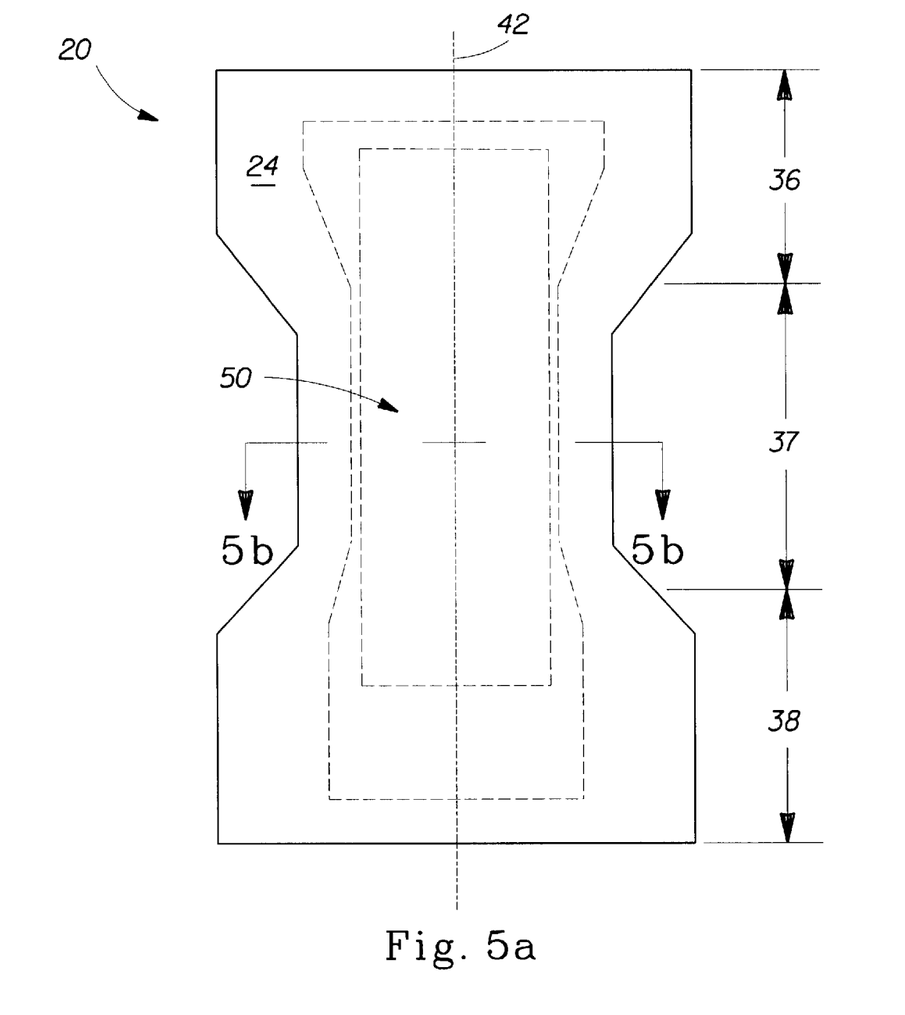
FIG. 5a is a plan view of a diaper having a wetness sensation member integrated with the topsheet.
Figure 5B:
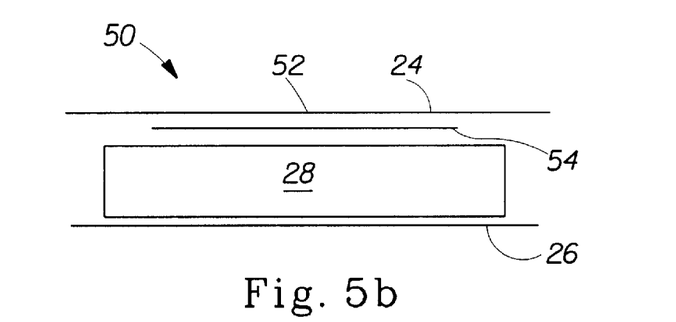

In an alternate embodiment shown in FIGS. 5a and 5b, the impermeable layer 54 of the wetness sensation member 50 is attached to the inner surface of the topsheet 24 such that at least a portion of the topsheet 24 forms the permeable layer 52 of the wetness sensation member 50. For this embodiment, the topsheet 24 is preferably elastically foreshortened to deflect the wetness sensation member 50 into contact with the wearer's skin. Alternatively, this embodiment may include a topsheet that is shorter in length than the backsheet, having the longitudinal ends of the topsheet contiguous with the longitudinal ends of the backsheet so that as the diaper is fitted around the wearer, the topsheet is forced into contact with the wearer's skin.

Regardless of the specific construction, the position and/or structure of the wetness sensation member 50 should enable the member to be wetted with urine and thereafter held in contact with the wearer's skin. The wetness sensation member is preferably disposed in at least a portion of the crotch region 37 of the diaper 20, centered about the longitudinal centerline 42. The wetness sensation member 50 may extend over a portion of the disposable absorbent article spanning less than one half of the length of the article or else extend a substantial part of the article spanning more than one half the length of the article. Furthermore, the wetness sensation member 50 is preferably coordinated with the wearer's urethra in order to cover the area in which urine initiates contact with the disposable absorbent article.

Figure 6A:
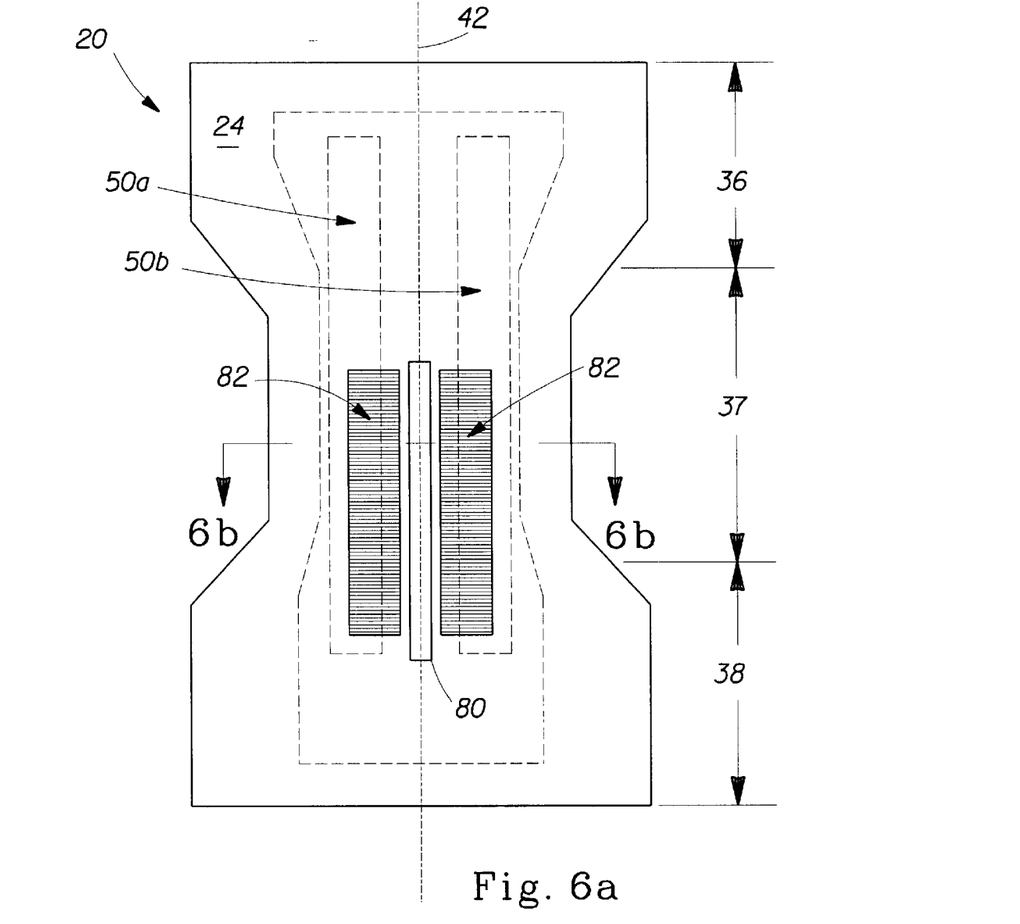
FIG. 6a is a plan view of a diaper having two wetness sensation members integrated with the topsheet and disposed parallel to and spaced apart from the longitudinal axis with an elongated slit opening interposed therebetween.
Figure 6B:
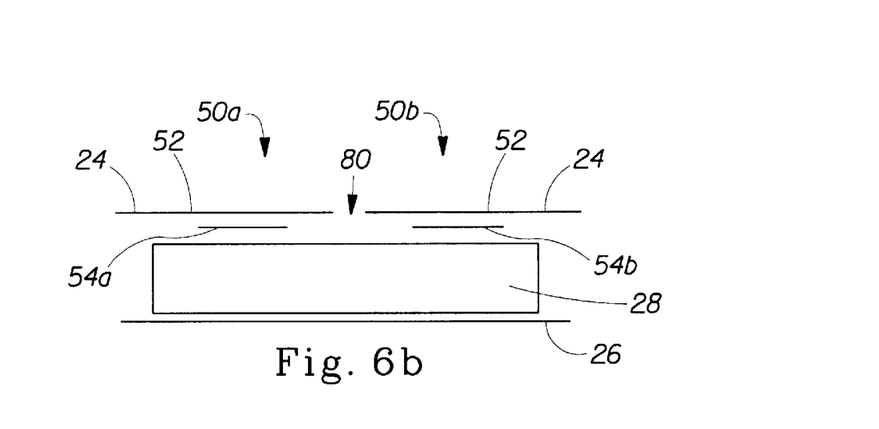

Absorbent articles according to the present invention may include a plurality of wetness sensation members disposed on the body-facing surface of the article. An example of an embodiment providing a plurality of wetness sensation members is shown in FIGS. 6a and 6b. Two impermeable layers 54a, 54b, are attached to the bottom surface of the topsheet 24 forming two wetness sensation members 50a, 50b. For this embodiment, the impermeable layers 54a, 54b are disposed between the topsheet and the absorbent core 28 so that the topsheet forms the permeable layers 52 of the wetness sensation members. The two impermeable layers 54a, 54b are disposed parallel to and spaced apart from the longitudinal centerline 42 of the diaper 20. The spacing is determined to allow enough liquid to pass through to the core so as to prevent flooding that can result in leakage of the absorbent article during urination, while at the same time enable enough liquid to flow and wick towards the impermeable layers forming the wetness sensation members. The spacing between the impermeable layers can be about 10 mm but can range from about 5 mm to about 15 mm and from about 8 mm and to about 12 mm. For this embodiment, the impermeable layers 54a, 54b are attached to the lower side of the topsheet 24 using adhesives, ultrasonic bonds, radio frequency bonds, or other suitable means. The attachment can comprise bonds covering the entire interface between the impermeable layers and the topsheet, spot bonds or bonds along the longitudinal and transverse edges of the impermeable layers. Although the embodiment described in FIGS. 6a and 6b show only two wetness sensation members, other absorbent article embodiments having three or more wetness sensation members are contemplated.

As shown in FIGS. 6a and 6b the spacing of the impermeable layers provide room for an elongated slit opening 80 in the topsheet 24. The elongated slit opening 80 is adapted to receive feces from the wearer and isolate the same from the wearer's skin. As shown, the slit opening 80 is preferably interposed between the wetness sensation members 50a, 50b along the longitudinal centerline 42 of the diaper 20. Elasticized regions 82 located adjacent to the slit opening 80 maintain alignment of the slit opening 80 with the wearer's anus during use. The elasticized regions 82 may also deflect the wetness sensation members 50a, 50b towards the wearer's skin to maintain contact therewith during use. Exemplary elasticized topsheets including elongated slit openings are disclosed in U.S. patent application Ser. No. 09/694,751, which is incorporated herein by reference. Alternatively, the impermeable layers 54a, 54b of the wetness sensation members 50a, 50b may be elastically foreshortened to provide benefits of the elasticized regions 82 disposed in the topsheet 24.

Figure 7A:
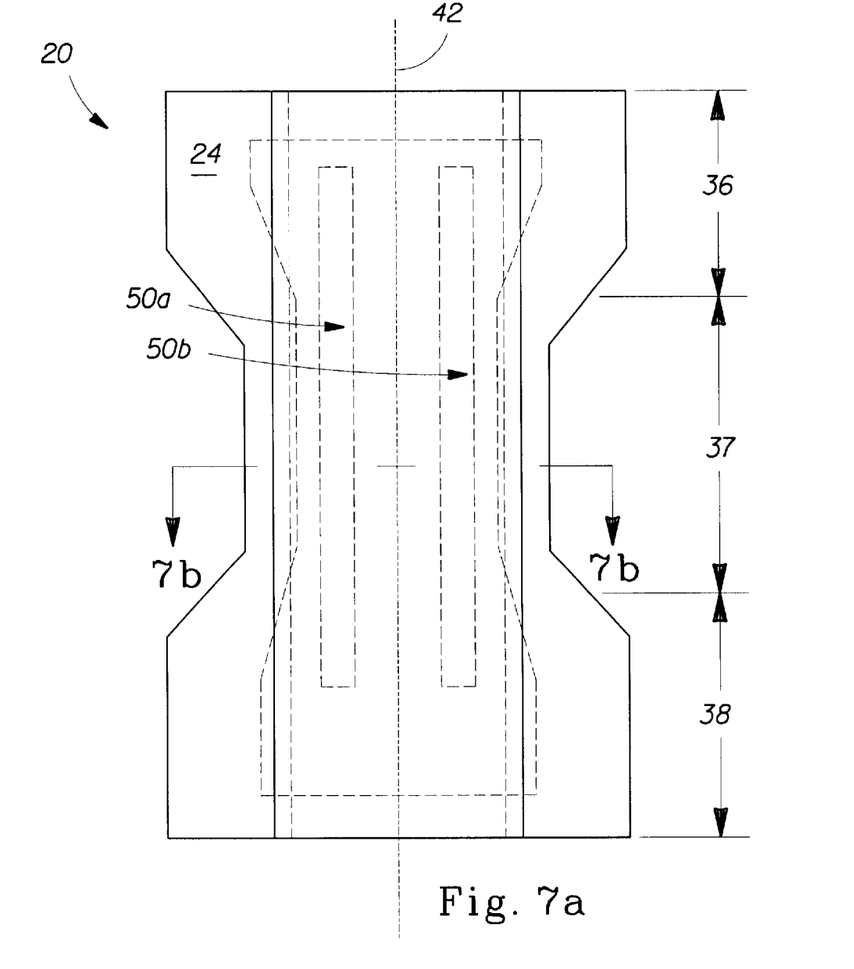
FIG. 7a is a plan view of a diaper having a Z-folded topsheet with two wetness sensation members integrated with the topsheet and disposed in the Z-folds in the topsheet.
Figure 7B:
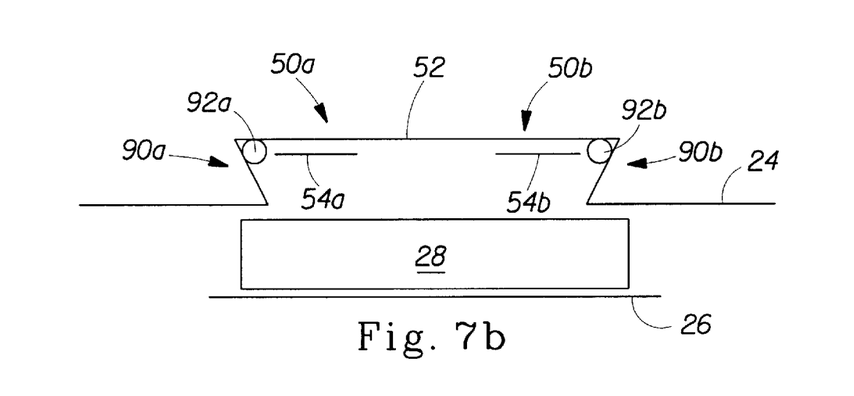

In another alternate embodiment shown in FIGS. 7a and 7b, the topsheet 24 forms the permeable layer 52 similar to the previous embodiment, however, the impermeable layers 54a, 54b are disposed in two parallel Z-folds 90 formed in the topsheet 24 along the longitudinal length of the diaper 20. The Z-folded topsheet may be attached to the underlying layers along the longitudinal edges of the topsheet 24 allowing the portion between the Z-folds of the topsheet 24 to float freely. Elastic elements 92 are disposed along the impermeable layers 54a, 54b in order to deflect the center portion of the Z-folded topsheet outward away from the absorbent core 28. The elastic elements 92 may be disposed along the outer edges of the impermeable layers 54a, 54b as shown in FIG. 7b, or alternatively, may be disposed in face-to-face relationship with the impermeable layers 54a, 54b. The combination of the Z-folded topsheet 24 and the elastic elements 92 maintains the wetness sensation members in contact with the wearer's skin in the event that the diaper sags or fits loosely around the wearer.

In order to prevent the portion of the topsheet between the Z-folds from being forced into the gluteal groove and from interfering with the barrier leg cuffs, the spacing between the Z-folds can be about 65 mm and can range from about 50 mm to about 90 mm. Further, in order to control deflection of the portion of the topsheet between the Z-folds, transverse bonds are produced between the Z-folds in the first waist region, the second waist region and the crotch region using adhesives, ultrasonic bonds, radio frequency bonds, or other suitable means in order to control deflection. These transverse bonds attach the Z-folded section to the body-facing surface of the topsheet and the section between the Z-folds to the underlying core.

In addition to incorporating the wetness sensation member with the topsheet, the wetness sensation member of the present invention may also be integrated with other components of the diaper such as the barrier leg cuffs. The barrier leg cuffs may be made from either permeable or impermeable material. In either case, the barrier leg cuff material may form one of the layers of the wetness sensation member.

Figure 8A:
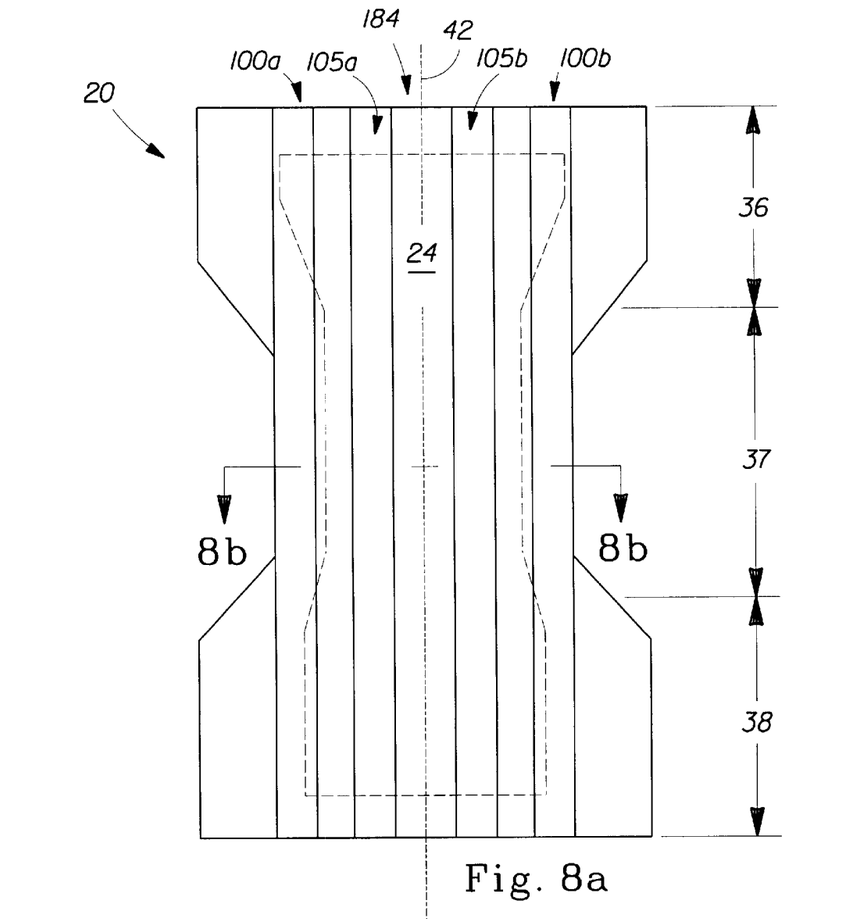
FIG. 8a is a plan view of a diaper with barrier leg cuffs including wetness sensation members integrated with the leg cuffs.
Figure 8B:
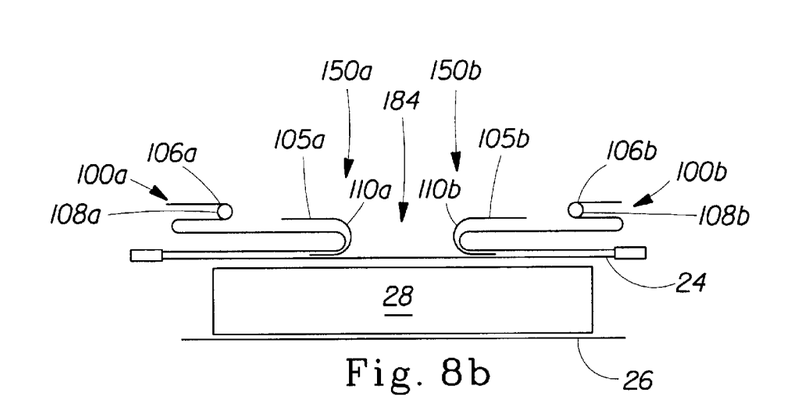

An example of wetness sensation members integrated with the barrier leg cuffs is shown in FIGS. 8a and 8b. The diaper 20 for this embodiment includes barrier leg cuffs 100a, 100b made from impermeable material. The barrier leg cuffs 100a, 100b extend along the longitudinal edges of the diaper 20 in a parallel arrangement disposed on the body-facing surface of the topsheet 24 leaving an exposed center portion 184 of the topsheet 24 therebetween. For the embodiment shown in FIGS. 8a and 8b, wetness sensation members 150a, 150b are incorporated with the barrier leg cuffs 100a, 100b such that the barrier leg cuff material provides the impermeable layer of the wetness sensation members. The permeable layer 110 can extend the length of the barrier leg cuffs, preferably the length of the crotch region 37 and the front waist region 36, and is disposed on portions of the cuff closest to the longitudinal axis 42 of the diaper 20 to increase the likelihood of becoming wetted during urination. As shown in FIGS. 8a and 8b, the barrier leg cuffs 100a, 100b include Z-folded configurations with inner folds 105a, 105b disposed near the longitudinal axis 42 of the diaper 20 leaving a center portion 184 of the topsheet 24 exposed. The Z-folded leg cuffs 100a, 100b also include outer folds 106a, 106b having elastic elements 108 disposed therein. During use, the elastic elements 108 deflect the leg cuffs away from the topsheet 24, towards the skin of the wearer.

The embodiments of wetness sensation members disclosed hereunder perform effectively when held in contact with the skin of the wearer. In order to ensure that contact is made with the wearer's skin during use, the body-facing portion of the wetness sensation members may include a topical adhesive or body adhering composition, which acts to hold the wetness sensation member in place during use. The topical adhesive may be applied to at least a portion of the body-facing surface of the wetness sensation member. However, the body adhering composition may also be integral with the material making up the body-facing layer of the wetness sensation member. Further, the body adhering composition may be disposed on any portion of the wetness sensation member contacting the skin of the wearer in any pattern or configuration including, but not limited to lines, stripes, dots, and the like.

Types of body adhering composition may include any one or more substances capable of releasably adhering to the skin of the wearer. Further, the body adhering composition may be in the form of a gel, lotion, film, web or the like. Examples of suitable body adhering compositions include adhesives, gelatin, petrolatum, waxes such as silicone or petroleum waxes, oils such as silicone or petroleum based oils, skin care compositions or ingredients thereof, as described below, and the like. Suitable topical adhesives include, but are not limited to, hydrogel or hydrocolloid adhesives such as acrylic based polymeric adhesives, and the like. (Some exemplary hydrogel and/or hydrocolloid adhesives are disclosed in U.S. Pat. Nos. 4,231,369; 4,593,053; 4,699,146; 4,738,257; and 5,726,250; each of which is incorporated by reference herein.) The topical adhesives may also include any "medical adhesive" which is compatible for use with biological tissue, such as skin. Acrylic medical adhesives suitable for use as body adhering compositions include adhesives available from Adhesive Research, Inc., of Glen Rock, Pa., under the designations MA-46, MA-312, "MTTM" High MVTR adhesive, and AS-17. Rubber-based medical adhesives, such as SB-2 from Adhesive Research Inc. may also be suitable. Other exemplary adhesives include Dow Corning Medical Adhesive (Type B) available from Dow Corning, Midland, Mich.; "MEDICAL ADHESIVE" from Hollister Inc., of Libertyville, Ill.; 3M Spray Adhesives #79, 76, 77 and 90 available from the 3M Corp. of St. Paul, Minn.; and "MATI-SOL" liquid adhesive available from Ferndale Laboratories of Ferndale, Mich. Other medical adhesives are described in U.S. Pat. Nos. 4,078,568; 4,140,115; 4,192,785; 4,393,080; 4,505,976; 4,551,490; 4,768,503 and polyacrylate and polymethacrylate hydrogel adhesives are disclosed in U.S. Pat. Nos. 5,614,586 and 5,674,275; the disclosure of each of which is incorporated by reference herein. Yet another exemplary adhesive comprising polyvinyl pyrrolidone and a multi-functional amine-containing polymer is disclosed in WO 94/13235A1. (The disclosure of each of these references is incorporated herein by reference.) Alternative body adhering means, which may be used in place of or in addition to those described above, include static electricity, suction, and the like. In any case, it is preferred that the body adhering composition permit vapors to pass (i.e., breathable), be compatible with the skin and otherwise skin friendly. Further, it is preferred that the body adhesive be at least partially hydrophobic, preferably 60%, more preferably 80%, by weight of the adhesive consist of hydrophobic components. However, hydrophilic adhesives are contemplated in certain embodiments of the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A wearable disposable absorbent article for wearing about a lower torso of a wearer and having a longitudinal axis, two laterally opposed article side edges extending between a laterally extending first waist end edge in a first waist region and a laterally extending second waist end edge in a second waist region, and a crotch region interposed therebetween, the wearable disposable absorbent article comprising:
    a backsheet;
    a topsheet joined to the backsheet and having a body-facing surface;
    an absorbent core disposed intermediate the backsheet and the topsheet; and
    a wetness sensation member held in close contact with the wearer's skin during use and integrated with the topsheet such that a portion of the topsheet covering a portion of the absorbent core forms a permeable body-facing layer of the wetness sensation member, the wetness sensation member also including an impermeable layer disposed between the permeable body-facing layer and the absorbent core in a face-to-face arrangement with the permeable body-facing layer and having two laterally opposed impermeable layer side edges, at least a portion of each of the two impermeable layer side edges being disposed laterally inwardly of the article side edges;
    wherein urine deposited by the wearer onto the wetness sensation member can penetrate through the permeable body-facing layer in a z direction away from the wearer to the impermeable layer and the impermeable layer prevents urine from passing completely through the wetness sensation member in the z direction and supports the movement of urine in an x-y plane such that the wearer's awareness of urination is enhanced.

2. The wearable disposable absorbent article as defined in claim 1 wherein the impermeable layer of the wetness sensation member is elastically foreshortened.

3. The wearable disposable absorbent article as defined in claim 1 wherein the topsheet is elastically foreshortened.

4. A wearable disposable absorbent article for wearing about a lower torso of a wearer and having a longitudinal axis, two laterally opposed article side edges extending between a laterally extending first waist end edge in a first waist region and a laterally extending second waist end edge in a second waist region, and a crotch region interposed therebetween, the wearable disposable absorbent article comprising:
    a backsheet;
    a topsheet joined to the backsheet and having a body-facing surface;
    an absorbent core disposed intermediate the backsheet and the topsheet; and
    a plurality of wetness sensation members disposed parallel to and spaced apart from the longitudinal axis and spaced apart from one another, each of the wetness sensation members being integrated with the topsheet such that a portion of the topsheet covering a portion of the absorbent core forms a permeable body-facing layer of each of the respective wetness sensation members, each of the wetness sensation members also including an impermeable layer disposed between the permeable body-facing layer and the absorbent core in a face-to-face arrangement with the permeable body-facing layer and having two laterally opposed impermeable layer side edges, at least a portion of each of the two impermeable layer side edges being disposed laterally inwardly of the article side edges;
    wherein urine deposited by the wearer onto each of the wetness sensation members can penetrate through the topsheet in a z direction away from the wearer to the impermeable layer and the impermeable layer prevents urine from passing completely through the wetness sensation member in the z direction and supports the movement of urine in an x-y plane to enhance the wearer's awareness that urination has occurred.

5. The wearable disposable absorbent article as defined in claim 4 wherein the impermeable layers of the wetness sensation members are elastically foreshortened.

6. The wearable disposable absorbent article as defined in claim 4 wherein the topsheet is elastically foreshortened.

7. A wearable disposable absorbent article having a longitudinal axis, a first waist region, a second waist region, and a crotch region interposed therebetween, the wearable disposable absorbent article comprising:
    a backsheet;
    a topsheet joined to the backsheet and having a body-facing surface;
    an absorbent core disposed intermediate the backsheet and the topsheet; and
    a plurality of wetness sensation members disposed parallel to and spaced apart from the longitudinal axis, each of the wetness sensation members being integrated with the topsheet such that a portion of the topsheet covering a portion of the absorbent core forms a permeable body-facing layer of each of the respective wetness sensation members, each of the wetness sensation members also including an impermeable layer disposed between the permeable body-facing layer and the absorbent core in a face-to-face arrangement with the permeable body-facing layer;

wherein urine deposited by a wearer onto each of the wetness sensation members can penetrate through the topsheet in a z direction away from the wearer to the impermeable layer and the impermeable layer prevents urine from passing completely through the wetness sensation member in the z direction and supports the movement of urine in an x-y plane to enhance the wearer's awareness that urination has occurred, and wherein the plurality of wetness sensation members are separated from one another by a spacing ranging from about 5 mm to about 15 mm.

8. A wearable disposable absorbent article having a longitudinal axis, a first waist region, a second waist region, and a crotch region interposed therebetween, the wearable disposable absorbent article comprising:

a backsheet;

a topsheet joined to the backsheet and having a body-facing surface;

an absorbent core disposed intermediate the backsheet and the topsheet; and a plurality of wetness sensation members disposed parallel to and spaced apart from the longitudinal axis, each of the wetness sensation members being integrated with the topsheet such that a portion of the topsheet covering a portion of the absorbent core forms a permeable body-facing layer of each of the respective wetness sensation members, each of the wetness sensation members also including an impermeable layer disposed between the permeable body-facing layer and the absorbent core in a face-to-face arrangement with the permeable body-facing layer;

wherein urine deposited by a wearer onto each of the wetness sensation members can penetrate through the topsheet in a z direction away from the wearer to the impermeable layer and the impermeable layer prevents urine from passing completely through the wetness sensation member in the z direction and supports the movement of urine in an x-y plane to enhance the wearer's awareness that urination has occurred, the topsheet is elastically foreshortened, and the elastically foreshortened topsheet comprises an elongated slit opening disposed along the longitudinal axis, the elongated slit opening aligns with a wearer's anus for receiving and isolating fecal material, and the impermeable layers are impermeable to liquid and permeable to vapor.

9. A wearable disposable absorbent article having a longitudinal axis, a first waist region, a second waist region, and a crotch region interposed therebetween, the wearable disposable absorbent article comprising:

a backsheet;

a topsheet joined to the backsheet and having a body-facing surface;

an absorbent core disposed intermediate the backsheet and the topsheet; and a plurality of wetness sensation members disposed parallel to and spaced apart from the longitudinal axis, each of the wetness sensation members being integrated with the topsheet such that a portion of the topsheet covering a portion of the absorbent core forms a permeable body-facing layer of each of the respective wetness sensation members, each of the wetness sensation members also including an impermeable layer disposed between the permeable body-facing layer and the absorbent core in a face-to-face arrangement with the permeable body-facing layer;

wherein urine deposited by a wearer onto each of the wetness sensation members can penetrate through the topsheet in a z direction away from the wearer to the impermeable layer and the impermeable layer prevents urine from passing completely through the wetness sensation member in the z direction and supports the movement of urine in an x-y plane to enhance the wearer's awareness that urination has occurred, and wherein the topsheet comprises two Z-folds parallel to the longitudinal axis and the impermeable layers are disposed within the two Z-folds.

10. The wearable disposable absorbent article as defined in claim 9 wherein the two Z-folds are separated by a spacing ranging from about 50 mm to about 90 mm.

11. The wearable disposable absorbent article according to claim 9, wherein the two Z-folds further comprise two elastic members disposed along the two impermeable layers.

12. The wearable disposable absorbent article as defined in claim 9 wherein each of the two Z-folds further comprises a first end, a second end opposite the first end, and a center disposed therebetween, and the first end, second end and center of each of the two Z-folds are discretely attached to the body-facing surface of the topsheet in the first waist region, the second waist region, and the crotch region, respectively.

* * * * *